(12) United States Patent
Sawada (10) Patent No.: US 6,673,605 B2
(45) Date of Patent: Jan. 6, 2004

(54) ESTABLISHED CELL LINE OF MICROGLIA

(75) Inventor: Makoto Sawada, Kasugai (JP)

(73) Assignee: Japan Science & Technology Corporation, Saitama (JP)

( * ) Notice: Subject to any disclaimer, the term of this patent is extended or adjusted under 35 U.S.C. 154(b) by 0 days.

(21) Appl. No.: 09/180,394

(22) PCT Filed: Mar. 5, 1998

(86) PCT No.: PCT/JP98/00949

§ 371 (c)(1),
(2), (4) Date: Mar. 8, 1999

(87) PCT Pub. No.: WO98/39415

PCT Pub. Date: Sep. 11, 1998

(65) Prior Publication Data

US 2002/0115206 A1 Aug. 22, 2002

(30) Foreign Application Priority Data

Mar. 5, 1997 (JP) .............................. 9-050448

(51) Int. Cl.[7] .......................... C12N 5/06; A01N 63/00
(52) U.S. Cl. ...................... 435/352; 435/353; 435/354; 435/368; 435/372; 435/325; 424/93.7
(58) Field of Search ................................ 435/325, 353, 435/354, 368, 352, 372; 424/93.7

(56) References Cited

FOREIGN PATENT DOCUMENTS

| JP | 1-172324 | 7/1989 |
|---|---|---|
| JP | 2-286621 | 11/1990 |
| JP | 5-49473 | 3/1993 |
| JP | 7-97330 | 4/1995 |
| WO | WO97/04789 | 2/1997 |

OTHER PUBLICATIONS

Sawada et al. Brain Research, 1990 (509), pp. 119–124.*
Sawada et al. Int. J. Dev. Neuroscience. 1995. vol. 13, No. 3/4, pp. 253–264.*
Alliot et al. Developmental Brain Research. 1996. (95), pp. 140–143.*
Ishihara et al. Experimental Neurology. 1993. 124:219–230.*
Sawada, M. et al. *Bulletin of the Japanese Neurochemical Society* 35:704–705 (1996).
Bitting, L. et al. *J. Biol. Chem.* 271:16084–16089 (1996).
Monning, U. et al. *J. Biol. Chem.* 270:7104–7110 (1995).
Suzumura, A. et al. *Bulletin of the Japanese Neurochemical Society* 28:52–53 (1989).
Mosser, D.D., et al. *BioTechniques* 22:150–161 (1997).
Eriksson, S. et al. *J. Virol. Methods* 59: 127–133 (1996).
Delagrave, S. et al. *Bio/Technology* 13:151–154 (1995).
Suzumura, Akio et al.: "Selective induction of interleukin–6 in mouse microglia by granulocyte–macrophage colony—stimulating factor." Brain Research, vol. 713, No. 1–2, 1996, pp. 192–198.
Sawada, Makoto, et al.: "Production of interleukin–5 by mouse astrocytes and microglia and culture." Neuroscience Letters, vol. 155, No. 2, 1993, pp. 175–178.
J. McLaurin et al., "Immortalization an characterization of rat microglical cells," Neuropathol. Appl. Neurobiol., vol. 21, p. 302–311 (1995).
J. Gehrmann, "Colony–stimulating factors regulate programmed cell death of rat microglia/brain macrophages in vitro," J. Neuroimmunology, 63 (1995) pp. 55–61.
H.G. Fischer et al., "Cyokine–Dependent K+ Channel Profile of AMicroglia at Immunologically Defined Functional States," Neuroscience, vol. 64, No. 1, pp. 183–191, 1995.
K. Nakajima et al., "Microgilla isolated from rat brain secrete a urokinase–type plasminogen activator," Brain Research, 577 (1992) pp. 285–292.

* cited by examiner

*Primary Examiner*—Sandra E. Saucier
*Assistant Examiner*—Vera Afremova
(74) *Attorney, Agent, or Firm*—Peter F. Corless; John B. Alexander; Edwards & Angell, LLP (57) ABSTRACT

The present invention relates to an established cell line of microglia having the following properties:

(a) form: having a macrophage-like or globular form in the presence of granulocyte-macrophage colony-stimulating factor. and in the absence of said factor, a branched form similar to branched microglia present in the brain, or both of the above forms;

(b) functional characteristics: having specific affinity for the brain, and
having a strong phagocytic ability; and (c) cell growth ability: growing depending on granulocyte-macrophage colony-stimulating factor. In particular, cell lines FERM BP-7061 and FERM BP-7062.

2 Claims, 6 Drawing Sheets

FORM OF GMI-RI

MACROPHAGE-LIKE (ARROW) AND GLOBULAR (ASTERISK) (IN THE PRESENCE OF GM-CSF)

FIG. 1A

BRANCHED (ARROW) (IN THE ABSENCE OF GM-CSF)

FIG. 1B

DIFFERENCE IN TISSUE SPECIFICITY BETWEEN THE CELL STRAIN OF MICROGLIA AND MACROPHAGES

SECTION FROM THE BRAIN OF A RAT INTO WHICH THE MICROGLIA WAS INJECTED VIA A BLOOD VESSEL.

FIG. 2A

SECTION FROM THE BRAIN OF A RAT INTO WHICH THE MACROPHAGE WAS INJECTED VIA A BLOOD VESSEL.

FIG. 2C

SECTION FROM THE LIVER OF A RAT INTO WHICH THE MICROGLIA WAS INJECTED VIA A BLOOD VESSEL.

FIG. 2B

SECTION FROM THE LIVER OF A RAT INTO WHICH THE MACROPHAGE WAS INJECTED VIA A BLOOD VESSEL.

MEASUREMENT OF ACTIVITY STAINING AND ENZYME ACTIVITY IN
BRAIN SECTION AFTER INJECTION OF LAC Z-INTRODUCED GMI-R1 CELLS

β-GALACTOSIDASE POSITIVE CELLS FOUND IN A SECTION OF THE BRAIN
FROM A RAT INTO WHICH GMI-R1 GENETICALLY MANIPULATED
TO EXPRESS LAC Z WAS INJECTED VIA A BLOOD VESSEL.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear    (iii) MOLECULE TYPE: Synthetic DNA    (xi) SEQUENCE DESCRIPTION: SEQ ID NO:1:

ATGGCAACTG TTCCTGAACT CAACT                              25

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear    (ii) MOLECULE TYPE: Synthetic DNA -continued (xi) SEQUENCE DESCRIPTION: SEQ ID NO:2:

CAGGACAGGT ATAGATTCTT TCCTTT                        26

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:3:

ATGAAGTTCC TCTCTGCAAG AGACT                         25

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:4:

CACTAGGTTT GCCGAGTAGA TCTC                          24

ESTABLISHED CELL LINE OF MICROGLIA

FIELD OF THE INVENTION

The present invention relates to an established cell line of microglia.

BACKGROUND OF THE INVENTION

Microglia is cells with macrophage-like properties in the central nervous system, which are cells not only functioning as immunocompetent cells in inflammatory reaction and viral infection and as phagocytes for removing cells but also playing a central role in a cytokine network in the central nervous system (Sawada, M. et al., Int. J. Dev. Neurosci., 13, 253–264, 1995). Recently, the microglia has been revealed to be essential for expression of high-level brain functions such as learning and memorization and considered to be specialized cells having a role specific for the brain.

There are quite a number of hereditary diseases in the nervous system, which occur due to various causative factors, for example by defect of a single enzyme etc. or by unknown reasons. Under these circumstances, supplementary therapy is used to cope with a large number of such disease.

A large number of studies have been made worldwide on the system of selective delivery to the brain. For introducing a gene into the brain in an animal, a method of using neuronphilic viruses as adenovirus vectors is devised, and a system for introducing a gene specifically into neurons is known (Kozarsky, K. F and Wilson, J. M, Curr. Opin. Genet. Dev., 3, 499–503, 1993). A method of using a retrovirus vector is also devised and has succeeded in introducing a gene into hepatic cells. blood cells etc. (Mullingan, R. C., Science 260, 926–932. 1993).

In the brain, however, the blood-brain barrier is present, so it is difficult to conduct supplementary therapy and to introduce an effective drug, and even if a substance (e.g. anticancer drug, DNA etc.) is introduced from a peripheral position, it cannot be introduced specifically into the brain. Therefore, there was no method other than direct injection of the substance by surgical operations.

As a method not involving invasive means such as surgical operations, there is a method of utilizing liposomes, and liposomes rendered capable of introduction into the brain relatively easily by changing their constitutional elements were developed by a Japanese group. However, even in this method too, incorporation of liposomes into the brain is as low as about 1% based on the injection amount, so this method cannot be said to be specific for the brain.

From the foregoing, it is necessary to prepare cells specific for the brain in order to transfer a substance to the brain.

Because microglia is brain cells, it is cited as a candidate for selectively transferring a substance to the brain specifically.

The microglia can be obtained by primary culture of brain cells. For this primary culture, however, the brain should be excised and purified for use, and primary culture usually requires a period of about 2 weeks, so the procedures are cumbersome. Further, the cells are difficult to proliferate during culture and hard to subculture, so after primary culture, it is extremely difficult to introduce a gene into the microglia to express it therein.

SUMMARY OF THE INVENTION

The object of the present invention is to provide an established cell line of microglia with specific affinity for the brain.

As a result of their eager study, the present inventors have succeeded in establishing a brain-specific cell line from cells after primary culture from brains of newborn mice and newborn rats, to arrive at the completion of the present invention.

That is, the present invention relates to an established cell line of microglia having the following properties:

(a) form: having a macrophage-like or globular form in the presence of granulocyte-macrophage colony-stimulating factor, and in the absence of said factor, a branched form similar to branched microglia present in the brain, or both of the above forms;

(b) functional characteristics: having specific affinity for the brain, and
having a strong phagocytic ability; and (c) cell growth ability: growing depending on granulocyte-macrophage colony-stimulating factor.

Further, the present invention relates to an established line of microglia comprising a gene or drug introduced into it.

DETAILED DESCRIPTION OF THE INVENTION

Hereinafter, the present invention is described in detail.

The established cell line of microglia of the present invention can be purified from mouse or rat brain cells after primary culture and then separated by the following means from this purified microglia. In addition, because the established cell line of microglia of the present invention is easily handled and has affinity for the brain, a gene or drug can be introduced into the established cell line of microglia and injected into peripheral blood vessels to express the gene in the brain or to deliver the drug to the brain specifically.

(1) Purification of Microglia

First, the meninges are removed from collected mouse or rat brains and divided into single cells by use of a pipette, nylon mesh etc. The mouse and rat are preferably newborn. The mouse includes, but is not limited to, C57BL6, C3H, ICR, Balb/c etc., and the rat includes, but is not limited to, Fisher, Wister, SD etc.

The resulting cells are plated on a usual animal cell culture medium (e.g. EMEM containing 10% FCS or Cs) and cultured for 10 to 14 days. The medium is exchanged with fresh one every 3 to 4 days.

Then, the cultured cells thus obtained are selected to prepare an established cell line in the subsequent step.

There are microglia called type I and type II, and type I is floating cells which are removed from the culture vessel upon mechanical stimulation of cells after primary culture (that is, by splashing the cells with a medium through a pipette, by shaking the culture vessel, etc.). Type II is cells (adherent cells) not floated by said mechanical stimulation. Since the microglia of the present invention belongs to type II, purified microglia can be selected in the following manner.

The adherent cells not floated by the above mechanical stimulation are treated with trypsin-EDTA, then divided into single cells, plated on a non-treated plastic dish (non-coat plastic vessel), and allowed to adhere to it. Generally, a conventional culture vessel is treated with chemicals so as to be positively charged, but a dish not subjected to this treatment should be used in order to obtain the adherent cells. After incubation in a $CO_2$ incubator at 37° C. for 1 hour, cells floating in the medium after mechanical stimulation are removed, and cells capable of proliferation on the vessel are recovered by Rubber Policeman etc., and the same procedure is repeated twice to give cells to be used in establishing a cell line of microglia.

Although the purified microglia thus obtained is of adequate purity, cell sorter etc. can also be used to further improve purity.

(2) Separation of Established Cell Line of Microglia

The purified microglia obtained in (1) above is plated on a vessel of about 10 cm diameter and cultured for 7 to 10 days in the presence of genetic recombinant granulocyte-macrophage colony-stimulating factor (rGM-CSF). After culture, the cells are recovered, and using limiting dilution, they are cultured for 4 to 10 weeks in the presence of rGM-CSF. Then, cells having formed a single colony in each well in the test plate are released by Rubber Policeman whereby the cloned cells are sorted and separated to finally give an established cell line of microglia.

The established cell line of microglia thus obtained has the following properties.

(a) Form

When observed after staining with a fluorescent pigment under a fluorescence microscope or without staining under a phase contract microscope, the cells have a macrophage-like or globular form in the presence of rGM-CSF, and in the absence of rGM-CSF, a branched form similar to branched microglia present in the brain. Otherwise the cells have both of the above forms.

(b) Functional Characteristics

Upon administration into an artery of a mouse, the established microglia of the present invention moves specifically to the brain, indicating that it has specific affinity for the brain. Further, the microglia upon stimulation with lipopolysaccharides produces interleukin-1 (IL-1) and interleukin-6 (IL-6). Upon stimulation with interferon γ, it produces IL-5. This property is different from that of macrophages because macrophages do not express IL-5 upon stimulation with IFN-γ. When the phagocytic ability of the cell line of the present invention is examined using incorporation of a fluorescent pigment as an indicator, it has a strong phagocytic ability. The established cell line of microglia of the present invention has a phagocytic ability which is hundreds to thousands times higher than that of astrocytes.

(c) Cell Growth Ability

Because the established microglia of the present invention is not proliferated after removal of rGM-CSF from the medium, it is proliferated depending on GM-CSF.

(3) Introduction of Gene into the Established Cell Line of Microglia

Introduction of a gene into the established cell line of microglia of the present invention is important f or expressing the gene specifically in the brain.

A desired gene can be obtained by known cloning means, and any commercially available gene can also be used, and the type of gene is particularly not limited.

The means for introducing a gene into the established cell line of microglia is as follows.

In the present invention, the established cell line of microglia may be cultured with a desired gene in a gene-introducing medium. They are cultured in a $CO_2$ incubator at 37° C. for 16 to 24 hours and further cultured together with rGM-CSF for 30 to 72 hours (preferably 48 hours) in a medium for culturing microglia.

In addition to the above-described means, the method of introducing the gene into the microglia includes conventional means such as the calcium phosphate method, DEAE dextran method, lipofection method, electroporation method, particle gum method etc.

Whether the cells having the gene introduced into them have reached the brain and whether the gene has been expressed can be confirmed in the following manner: The cells to be introduced are stained with a fluorescent pigment specific for phagocytes. After introduction of the cells into an animal, the brain is excised and frozen, from which a section of about 8 microns in thickness is prepared from the brain and examined for fluorescent cells under a fluorescence microscope, or the section is activity-stained with a substrate for the introduced gene.

The cells can also be confirmed using magnetic nuclear resonance image (MRI), positron emission tomography (PET) etc. For example, contrast media etc. for MRI may be incorporated into the cells which are then injected into an animal So that the cells can be monitored in the animal. According to these methods, it is not necessary to kill the animal, and the cells can be monitored easily in a non-invasive manner.

According to the present invention, there can be provided an established cell line of microglia having specific affinity for the brain. The established cell line of microglia of the present invention is useful not only as carriers for introducing a gene into the brain but also as carriers for introducing chemical substances such as drug etc. specifically into the brain.

EXAMPLES

Hereinafter, the present invention is described in more detail by reference to Examples. However, the scope of the present invention is not limited to the Examples.

Example 1

Separation of Established Clone of Microglia (1) Isolation of Microglia

Brains were excised from newborn mice (C57BL6, op/op) and newborn rats (Fisher), and meninges were removed in an ice-cold microglia culture medium (referred to as Mi medium; Eagle's MEM containing 10% bovine serum, 0.2% glucose and 5 μg/ml bovine insulin). The cells of meninges were divided into single cells with a Pasteur pipette or nylon mesh and then cultured in Mi medium. For the cells from the mouse brains, 20 ml Mi medium was used per one cell, and for the cells from the rat brains, 40 ml Mi medium was used per one cell, and the former cells were incubated in 2 culture vessels of 10 cm diameter and the latter cells in 4 culture vessels of 10 cm diameter in a $CO_2$ incubator (5% $CO_2$, 95% air) at 37° C. for 10 to 14 days. The medium was exchanged with fresh one every 3 to 4 days.

When phase-bright round cells (PBRCs) appeared, the PBRCs were removed by mechanical shaking, and the remaining cells were removed with 200 U/ml trypsin-0.02% EDTA and incubated in a non-coat plastic vessel at 37° C. for 30 minutes. The cells which adhered to the non-coat plastic vessel were washed twice with M1 medium, and the cells were then removed and recovered. The same procedure was repeated further twice to give purified microglia.

(2) Separation of Clones $1 \times 10^5$ purified microglia cells obtained in (1) above were plated on a 10 cm vessel and cultured for 7 days in Mi medium in the presence of rGM-CSF (Genzyme).

The cells were recovered and counted, and clones were obtained from the cells in the following manner using limiting dilution. The cells were put to each well on a 96-well plate (Falcon) at a density of 0.5 cell/well (in 100 μl) and cultured for about 3 weeks in the presence of 2 ng/ml mouse gene recombinant GM-CSF (Genzyme). Each well was examined for the presence of the clone, and the target clones were separated.

As a result, five kinds of established microglia (Ra2, GMI-M6-1, GMI-M6-3, GMI-M5-2, GMI-MF11) derived from the mouse brains and one kind (GMI-R1) from the rat brains were obtained.

Among these, the established cell lines of microglia, Ra2 and GMI-R1, have been designated "mouse microglia Ra2" and "rat microglia GMI-R1" and deposited as FERM BP-7061 and FERM BP-7062 respectively with the National Institute of Bioscience and Human-Technology, Agency of Industrial Science and Technology, Japan.

The properties of the resulting clones were then examined.

(a) Form

Figure 1A:
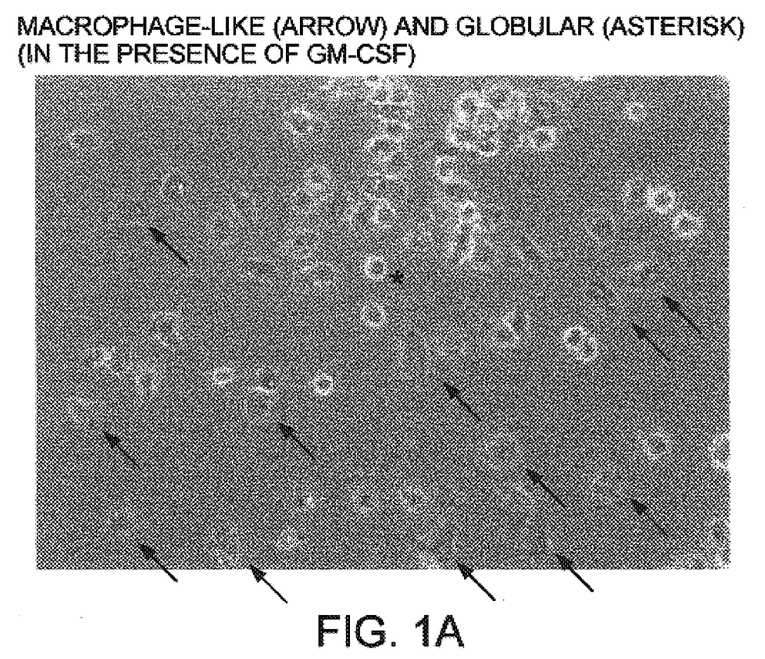
FIG. 1A is a photograph showing the form of the established cell line of microglia of the present invention in the presence of granulocyte-macrophage colony-stimulating factor.
Figure 1B:
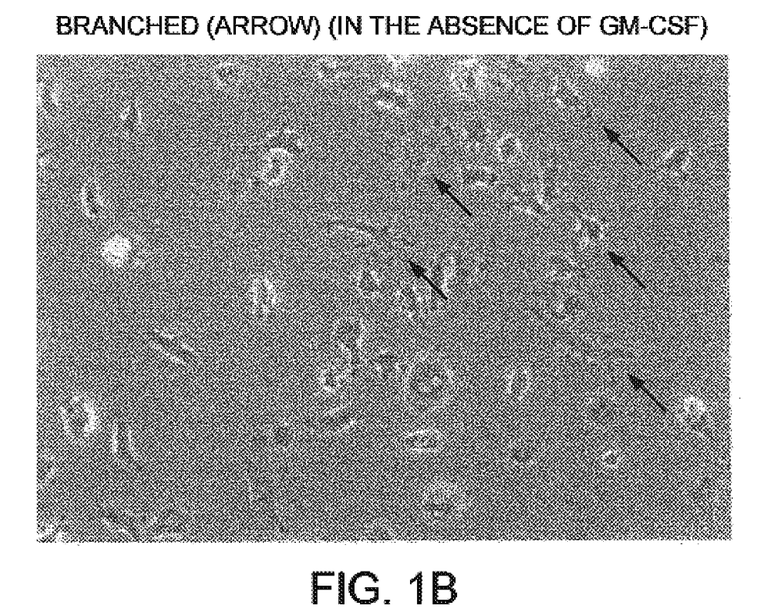
FIG. 1B is a photograph showing the form of the established cell line of microglia of the present invention in the absence of granulocyte-macrophage colony-stimulating factor.

When GMI-RI incubated in the presence or absence of rGM-CSF was observed under a phase contrast microscope, it had a macrophage-like or globular form in the presence of rGM-CSF (FIG. 1A) or a branched form in the absence of rGM-CSF (FIG. 1B).

(b-1) Functional Characteristics (Affinity for the Brain)

The established cell line of microglia GMI-R1 of the present invention was allowed to adhere to a plastic vessel. Separately, a fluorescent pigment PKH26 (Zynaxis) prepared in a phagocyte-staining solution (Diluent B, Zynaxis) and 10% serum were mixed at a ratio of 1:1 and added to the above vessel, and GMI-RI was stained with the fluorescent pigment at 37° C. for 15 minutes (Ishihara, S., Sawada, M. et al., Exp. Neurol., 124, 219–230, 1993).

The cells were recovered and $2 \times 10^6$ cells were injected into an artery in the armpit of each of 5-week-old rats from the same strain (Fisher). 48 hours and 1, 2, and 3 weeks after injection, each organ was excised from the rats and frozen in a solution of OCT (Miles Inc.).

Microglia GMI-R1, and macrophages isolated for comparison from the abdomen of a rat of the same strain (Fisher) by washing it with cold PBS, were labeled respectively with a fluorescent pigment specific for phagocytes and then injected into arteries of rats, and tissue sections were prepared for examination of the tissues.

Figure 2A:
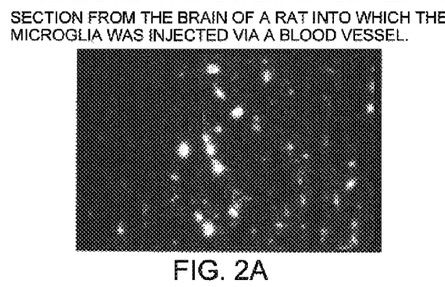
FIG. 2 is a photographic series showing the difference in tissue specificity between the established cell line of microglia of the present invention and macrophages wherein (A) is a photograph of the brain of a rat into which the microglia was injected via a blood vessel, (B) is a photograph of the liver of a rat into which the microglia was injected via a blood vessel, (C) is a photograph of the brain of a rat into which the macrophage was injected via a blood vessel, (D) is a photograph of the liver of a rat into which the macrophage was injected via a blood vessel
Figure 2B:
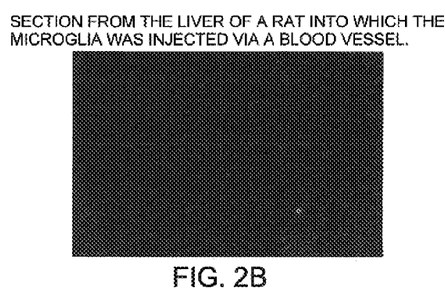
Figure 2C:
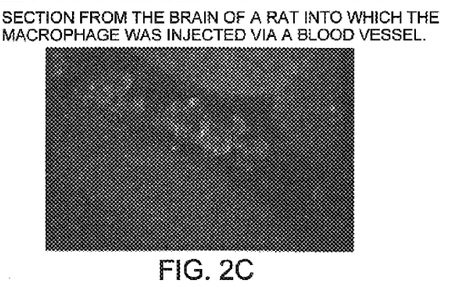
Figure 2D:
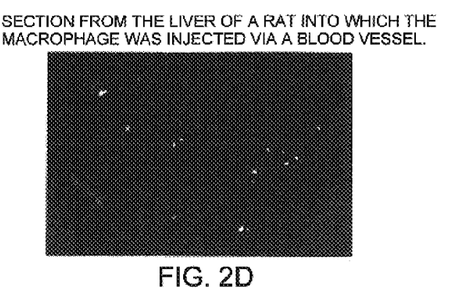

After the established microglia of the present invention was injected, many fluorescent cells were observed in normal brain cells (FIG. 2A) but not observed in the liver (FIG. 2B). On the other hand, after the macrophages were injected, fluorescent cells were hardly observed in normal brain cells (FIG. 2C), while many fluorescent cells were observed in the liver (FIG. 2D).

Accordingly, the established cell line of microglia of the present invention possessed specific affinity for the brain.

(b-2) Functional Characteristics (Ability to Produce IL-1 and IL-6)

$2 \times 10^6$ Ra2 cells were plated onto a 6 cm culture vessel, and total RNA was extracted from the cells stimulated with lipopolysaccharides for 12 hours or from the cells not stimulated, and 2 mg of the RNA was used to prepare a cDNA mixture by reverse transcriptase (BRL). PCR was carried out using the resulting cDNA as a template, where an IL-1 specific synthetic primer and IL-6 specific synthetic primer having the following sequences were used.

IL-1 specific synthetic primer (Sawada et al., Int. J. Dev. Neurosci, 13, 253–264, 1995):

Sense chain: 5'-ATGGCAACTGTTCCTGAACTCAACT-3' (SEQ ID NO: 1)

Antisense chain: 5'-CAGGACAGGTATAGATTCTTTCCTTT-3' (SEQ ID NO: 2)

IL-6 specific synthetic primer (Sawada et al., Brain Res. 583, 296–299, 1992):

Sense chain: 5'-ATGAAGTTCCTCTCTGCAAGAGACT-3' (SEQ ID NO: 3)

Antisense chain: 5'-CACTAGGTTTGCCGAGTAGATCTC-3' (SEQ ID NO: 4)

In PCR, 30 cycles each consisting of reaction at 55° C. for 1 minute, 72° C. for 2 minutes and 94° C. for 1 minute were carried out (Omnigene from HYBAID Co., Ltd. was used).

After PCR, the amplification product was subjected to agarose gel electrophoresis to examine gene expression.

Figure 3:
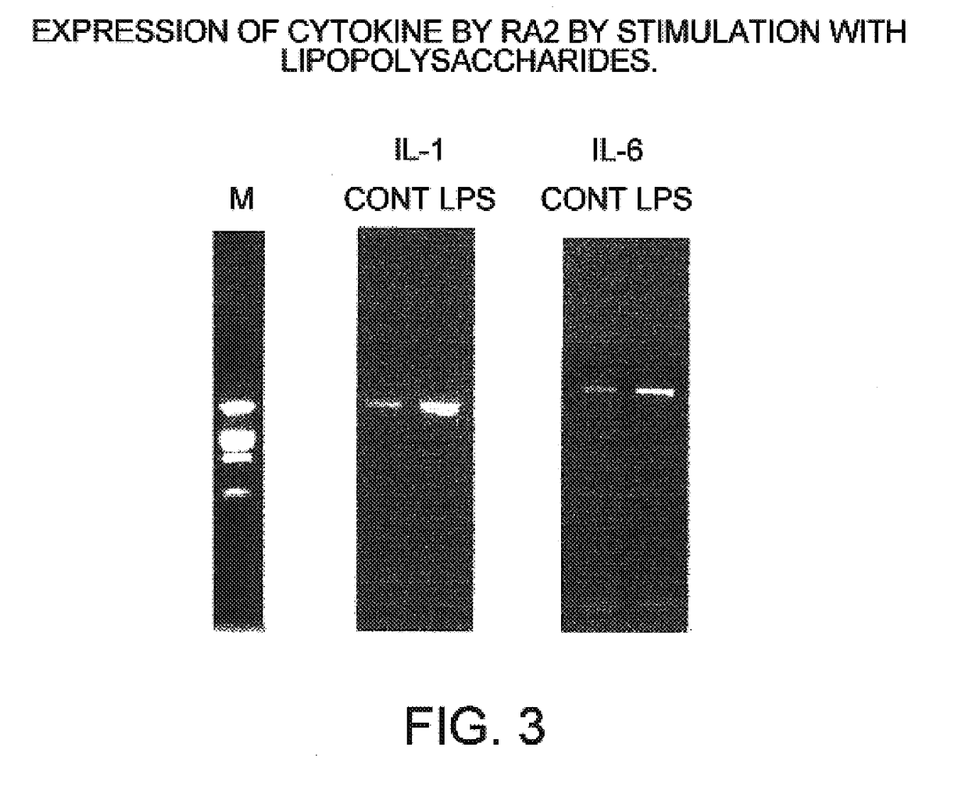
FIG. 3 shows electrophoresis indicating cytokine expression by stimulation with lipopolysaccharides.

As a result, it was found that Ra2 increased expression of IL-1 and IL-6 (FIG. 3, "LPS" lanes). In FIG. 3, "M" is a molecular marker and "cont" is control (not stimulated).

Production of IL-1 and IL-6 was also confirmed by ELISA. Further, a culture supernatant of the established microglia of the present invention after stimulation with lipopolysaccharides was added to MH60 cells growing depending on IL-6 or to D10 cells growing depending on IL-1, followed by incubation, and whether the MH60 cells and D10 cells were proliferated or not was examined.

As a result, it was found that both the cells were proliferated in the presence of the culture supernatant of the established microglia of the present invention stimulated with the lipopolysaccharides.

Figure 4A:
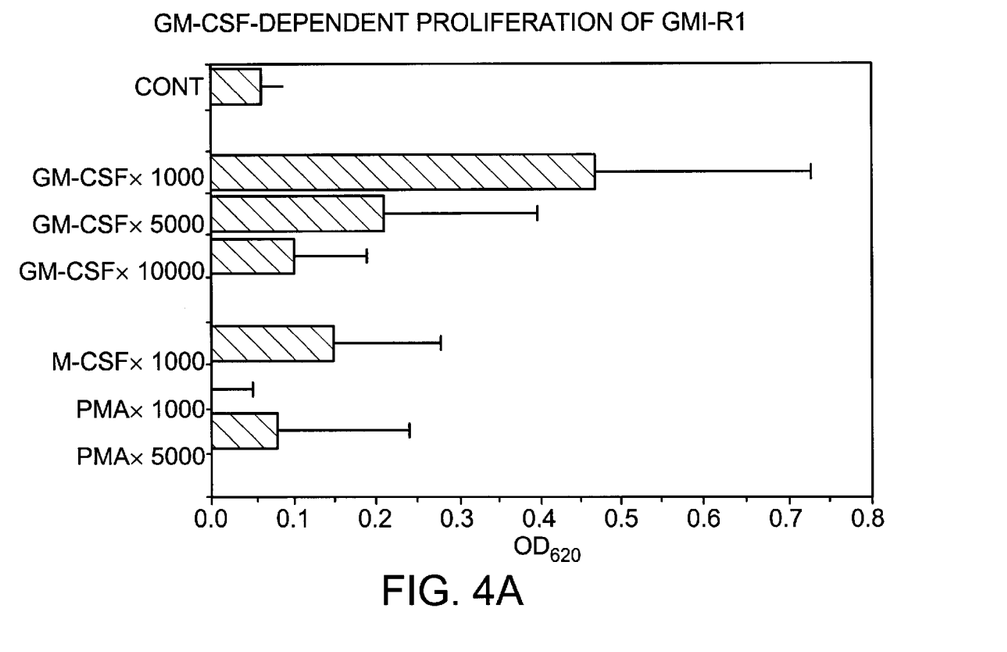
FIG. 4A shows a bar chart of GM-CSF dependent proliferation of the established cell line of microglia of the present invention.

(a) Cell Growth Ability $5 \times 10^4$ GMI-R1 cells were plated on a 96-well test plate, and 2 μg/ml rGM-CSF was added to it so as to be diluted 1000-, 5000- and 10000-fold respectively, and the cells were incubated for 4 days and then subjected to MTT assays. 400 μ/ml human M-CSF (The Green Cross Corporation) was diluted 1000-fold and 0.1 mg/ml PMA (phorbol myristate acetate) was diluted 1000- or 5000-fold, and these were used as the control (FIG. 4A).

Figure 4B:
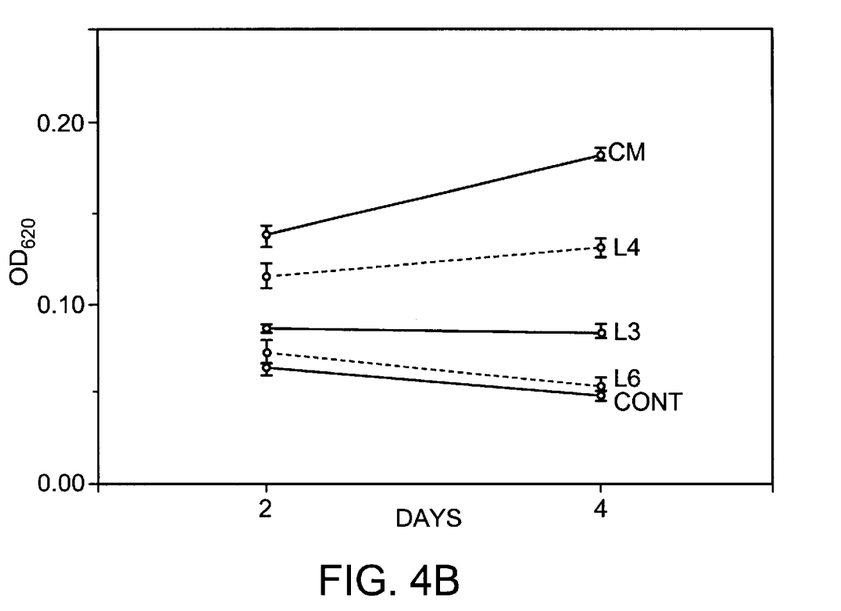
FIG. 4B shows a chart of GM-CSF dependent proliferation of the established cell line of microglia of the present invention.

Separately, rGM-CSF diluted 5000-fold, and 100 μ/ml each of mouse IL-3, IL-4 and IL-6 (any of which were produced by Genzyme), were examined in a comparative test. Two or four days after addition of the respective reagents, MTT assays were carried out (FIG. 4B).

As a result, it was found that GMI-R1 was proliferated depending on rGM-CSF.

Example 2

Introduction of a Gene into the Microglia of the Invention

Vector ptkβ (Clonetech) for expression of lac Z gene derived from *E. coli* and DOTAP lipid (Boehringer-Mannheim) were mixed at a final concentration of 1 μg/ml. The mixture was mixed with a serum-containing medium, then added to the established microglia of the present invention and incubated for 16 hours. As the control, the established microglia of the invention into which the gene was not introduced, and macrophages obtained in the same manner as in Example 1, were used.

Then, the cells were further cultured for 48 hours in a usual medium (EMEM plus 10% FCS) and then stained with the fluorescent pigment as described in Example 1 (b-1) in order to examine whether the gene was delivered to and expressed in the brain, as follows: An artery in the left armpit of a mature rat (250 to 300 g) under anesthesia with Nembutal was exposed. After hemostatic treatment, a cannula was inserted into the artery and used to inject 1 to $2 \times 10^6$ cells into the rat. After injection, the incision site was sutured and the rat was allowed to recover.

48 hours after the cells were injected, the brain was excised from the rat and 3 successive frozen sections of the brain were prepared and observed respectively under a fluorescence microscope. Further, staining and quantification of β-galactosidase activity was carried out in the following manner.

One of the three sections was fixed in 0.5% glutaraldehyde and subjected to activity staining with Xgal as substrate according to the method of Lim et al. (Bio Techniques 7, 576–579, 1989). To quantify the activity, one of the sections was homogenized in a dissolving buffer by ultrasonication and examined for its activity with a commercial kit (Galacto Light: Boehringer-Mannheim).

Figure 5:
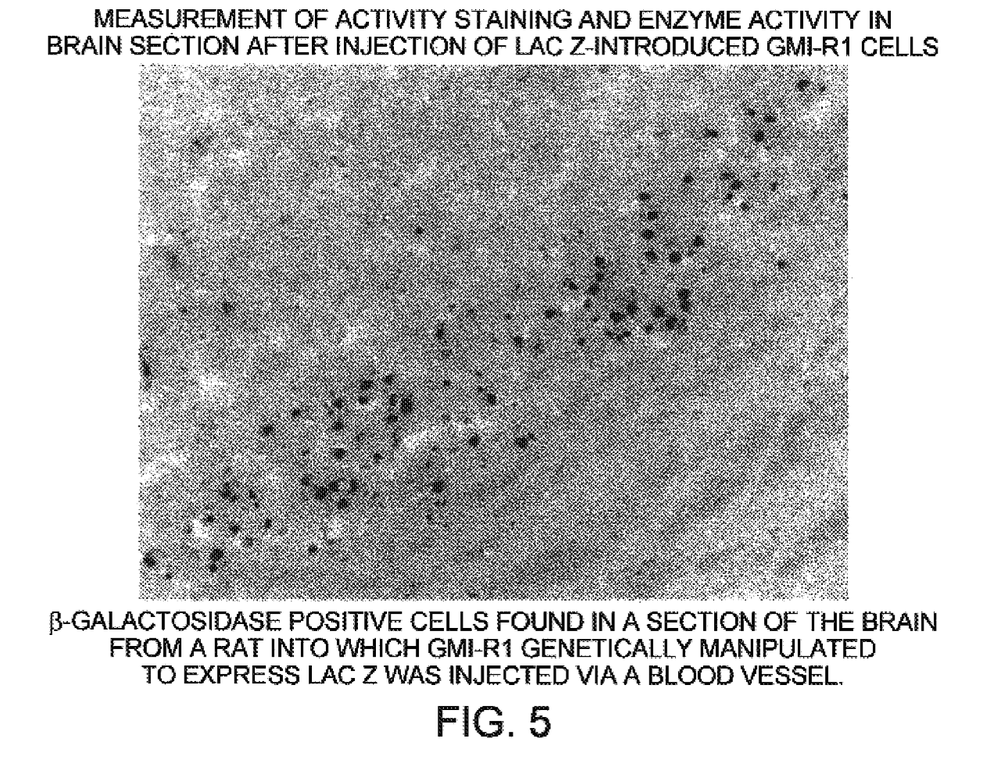
FIG. 5 is a photograph indicating gene expression in a rat brain (morphology of the cells).
Figure 6:
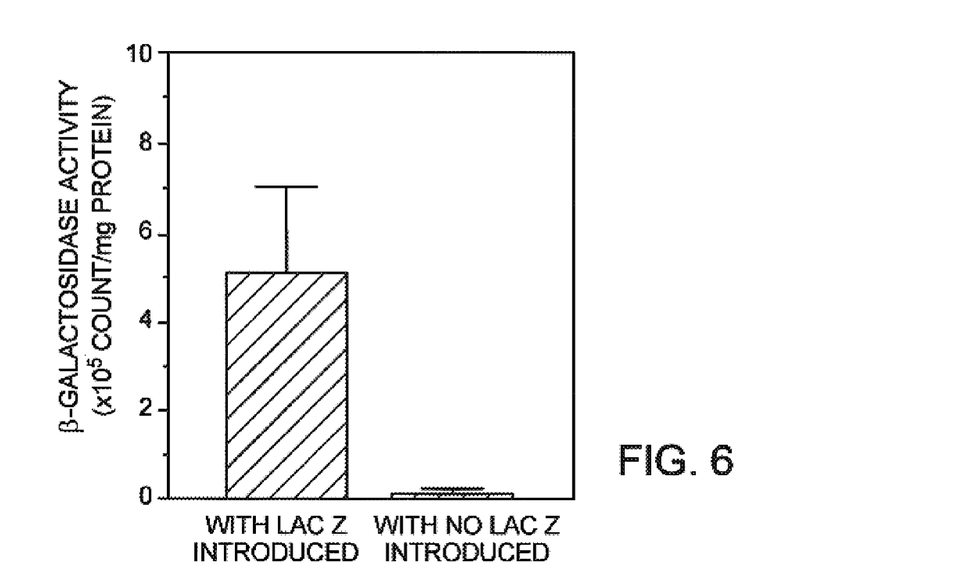
FIG. 6 shows gene expression on a rat brain.
Figure 7:
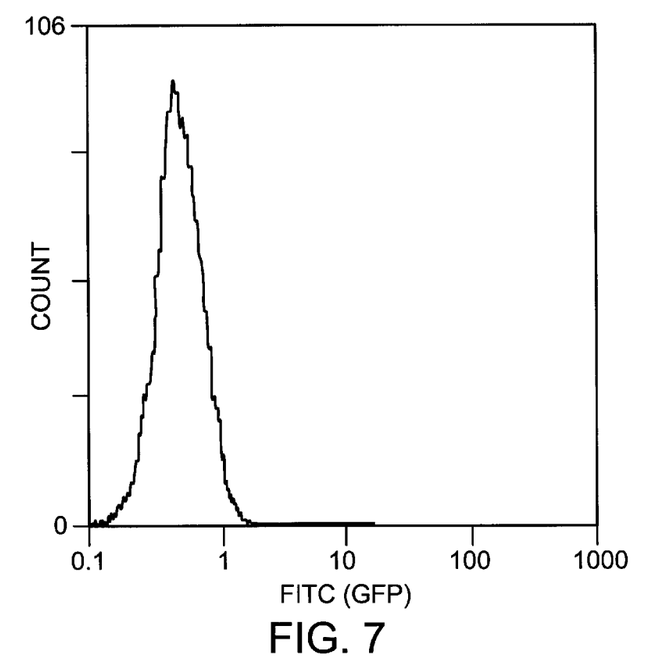
FIG. 7 shows the result of FACS analysis of a cell wherein a gene is not introduced.
Figure 8:
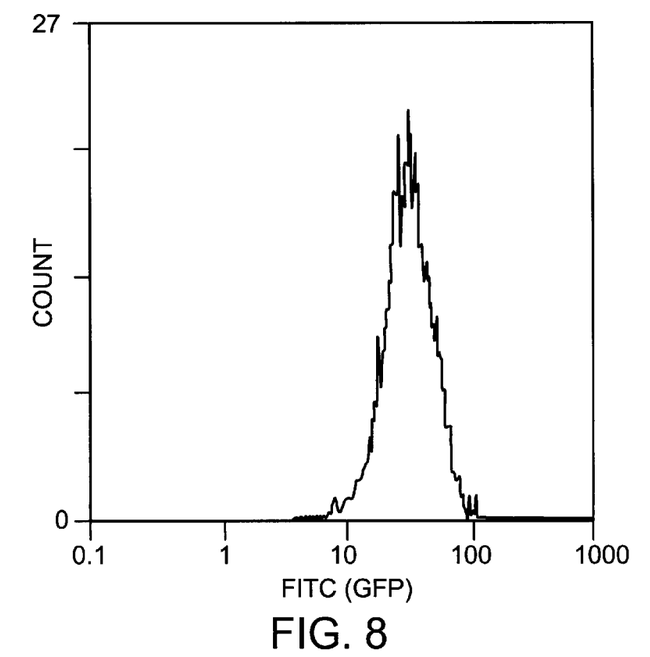
FIG. 8 shows the result of FACS analysis of a cell wherein a GFP gene is introduced.

As a result, it could be confirmed that in case the gene was introduced into the established microglia of the present invention, lacZ-positive cells were present in the section from the rat brain (FIG. 5). Further, as a result of quantification of β-galactosidase activity by the chemiluminescence method, considerable higher activity was detected in the rat brain section into which the *E. coli*-derived gene lac Z expression vector was introduced than the counterpart into which the gene was not introduced (FIG. 6).

Example 3

Introduction of Chemical Substance into the Microglia of the Invention, and Specific Introduction Thereof into the Brain The fluorescent pigment PKH26 used in Example 1 forms granules in diluent B. The microglia cell strain of the present invention incorporates these granules specifically and transfers them to the brain, so the fluorescent pigment PKH26 was used as a model of chemical substance (anti-tumor drug).

As a result, when the established cell line of microglia of the present invention was introduced, many fluorescent cells were observed in normal brain cells but not observed in the liver. It therefore follows that the microglia of the present invention transfers the chemical substance (drug) into the brain specifically.

What is claimed is:

1. A biologically pure cell line of microglia having all identifying characteristics of the cell line Ra2 (FERM BP-7061) which is capable of passing through blood-brain barrier.

2. A biologically pure cell line of microglia having all identifying characteristics of the cell line GMI-R1 FERM BP-7062) which is capable of passing through blood-brain barrier.

* * * * *